United States Patent
Putnins

(10) Patent No.: US 11,607,026 B2
(45) Date of Patent: Mar. 21, 2023

(54) DEVICE FOR DELIVERY OF SKIN CARE COMPOSITION

(71) Applicant: Johnson & Johnson Consumer Inc., Skillman, NJ (US)

(72) Inventor: Matthew Eric Putnins, Ridgewood, NJ (US)

(73) Assignee: Johnson & Johnson Consumer Inc., Skillman, NJ (US)

(*) Notice: Subject to any disclaimer, the term of this patent is extended or adjusted under 35 U.S.C. 154(b) by 899 days.

(21) Appl. No.: 14/291,508

(22) Filed: May 30, 2014

(65) Prior Publication Data

US 2015/0342900 A1    Dec. 3, 2015

(51) Int. Cl.
  *A45D 37/00*    (2006.01)
  *A61K 9/70*    (2006.01)
  *A61K 8/02*    (2006.01)
  *A61Q 19/00*    (2006.01)

(52) U.S. Cl.
  CPC ............ *A45D 37/00* (2013.01); *A61K 8/0208* (2013.01); *A61K 9/7084* (2013.01); *A61Q 19/00* (2013.01)

(58) Field of Classification Search
  CPC .......... A61K 9/70; A61K 8/02; A61K 9/7084; A61K 9/703; A61M 35/00; A61M 35/006; A45D 37/00; A45D 40/00; A47L 13/17; B32B 1/00
  USPC ......................................... 604/290, 307, 306
  See application file for complete search history.

(56) References Cited

U.S. PATENT DOCUMENTS

| | | | |
|---|---|---|---|
| 2,098,312 A | 11/1937 | Scholl | |
| 2,115,237 A | 4/1938 | Scholl | |
| 2,120,465 A | 6/1938 | Hartley | |
| 2,123,121 A | 7/1938 | Schrader | |
| 2,280,506 A | 4/1942 | Betts | |
| 2,575,133 A | 11/1951 | Scholl | |
| 2,633,127 A | 3/1953 | Scholl | |
| 2,918,062 A | 12/1959 | Scholl | |
| 4,765,478 A * | 8/1988 | Bringloe | A61F 15/001 206/440 |
| 4,849,224 A * | 7/1989 | Chang | A61K 9/703 424/434 |
| 4,858,604 A * | 8/1989 | Konishi | A61F 13/0203 602/57 |
| 4,956,181 A * | 9/1990 | Bayer | A61K 9/703 424/447 |
| 5,096,715 A * | 3/1992 | Sinclair | A61K 9/48 424/443 |

(Continued)

FOREIGN PATENT DOCUMENTS

| | | |
|---|---|---|
| DE | 19812887 A1 | 9/1999 |
| EP | 0963715 A2 | 12/1999 |

(Continued)

OTHER PUBLICATIONS

EP search report dated May 6, 2020, for EP application 20151821.4.

*Primary Examiner* — Nicholas J. Weiss
*Assistant Examiner* — Gabriella E Burnette

(57) ABSTRACT

A novel device and method for delivering a liquid containing an active ingredient to a treatment site on the skin is disclosed. The device is useful for treating lesions or abnormal skin features such as corns, warts, calluses, bunions, actinic keratoses and hard hyperkeratotic skin as is often found on the face, arms, legs or feet.

10 Claims, 2 Drawing Sheets

(56) References Cited

U.S. PATENT DOCUMENTS

| | | | |
|---|---|---|---|
| 5,098,421 A | 3/1992 | Zook | |
| 5,141,750 A * | 8/1992 | Lee | A61K 9/7069 |
| | | | 424/448 |
| 5,271,940 A * | 12/1993 | Cleary | A61K 9/703 |
| | | | 424/443 |
| 5,462,743 A | 10/1995 | Turner et al. | |
| 5,641,507 A | 6/1997 | Devillez | |
| 5,662,925 A * | 9/1997 | Ebert | A61K 9/703 |
| | | | 424/447 |
| 5,962,011 A | 10/1999 | Devillez et al. | |
| 6,070,392 A * | 6/2000 | Berman | A45D 40/0087 |
| | | | 53/127 |
| 6,255,552 B1 | 7/2001 | Cummings et al. | |
| 6,267,984 B1 * | 7/2001 | Beste | A61K 9/0014 |
| | | | 424/447 |
| 6,471,986 B1 | 10/2002 | Cline et al. | |
| 6,547,468 B2 * | 4/2003 | Gruenbacher | A47K 7/03 |
| | | | 401/132 |
| 6,756,052 B1 * | 6/2004 | Koch | A61K 31/485 |
| | | | 424/448 |
| 7,523,821 B2 * | 4/2009 | Assie | A61F 15/001 |
| | | | 15/104.93 |
| 7,650,995 B2 * | 1/2010 | Assie | A61F 15/001 |
| | | | 206/440 |
| 10,610,416 B2 * | 4/2020 | Kirsch | A61F 13/0226 |
| 2002/0172712 A1 | 11/2002 | Drizen et al. | |
| 2004/0013716 A1 | 1/2004 | Gale et al. | |
| 2004/0166147 A1 * | 8/2004 | Lundy | A61K 9/703 |
| | | | 424/449 |
| 2005/0228340 A1 * | 10/2005 | Cleary | A61M 37/0015 |
| | | | 604/46 |
| 2006/0204561 A1 | 9/2006 | Muhammad et al. | |
| 2006/0235351 A1 | 10/2006 | Matsumura et al. | |
| 2011/0098620 A1 | 4/2011 | Dever | |
| 2013/0345650 A1 * | 12/2013 | Amirouche | A61M 35/00 |
| | | | 604/305 |
| 2015/0342900 A1 * | 12/2015 | Putnins | A61P 17/12 |
| | | | 604/290 |
| 2019/0290597 A1 * | 9/2019 | Zhang | A61P 11/06 |

FOREIGN PATENT DOCUMENTS

| | | |
|---|---|---|
| GB | 2197590 A | 5/1988 |
| JP | 08-509200 | 7/1990 |
| JP | 09-506803 | 6/1995 |
| JP | 9-124468 | 5/1997 |
| JP | 2010-538682 | 10/2008 |
| WO | WO1998/58631 A1 | 12/1998 |

* cited by examiner

DEVICE FOR DELIVERY OF SKIN CARE COMPOSITION

FIELD OF THE INVENTION

The present invention relates generally to devices for the delivery of skin care compositions, especially active ingredients and cosmetic ingredients. More specifically, the invention is a padded device for delivery of active ingredients to corns, calluses and warts.

BACKGROUND OF THE INVENTION

Devices for transdermal or percutaneous drug delivery are known. Such devices are typically characterized by delivering an amount of a drug, e.g. nitroglycerin, estrogen, estradiol, corticoid, levonorgestrel, etc. to the patient's skin at a rate controlled by the device. Subsequently, the drug is delivered systemically to the intended site of treatment within the body.

Although effective for their intended use, such controlled release devices have limited utility for providing the kind of treatment which requires maximum delivery of the drug or active ingredient for local skin conditions, for example, lesions or abnormal skin features such as corns, warts, calluses, bunions, actinic keratoses and hard hyperkeratotic skin as is often found on the face, arms, legs or feet. Other types of delivery devices such as medicated plasters have been used for corns, warts, calluses, etc. However, the amount of active ingredient that can be delivered by such plasters is limited by the dimensions of the plaster and solubility of the active ingredient in the plaster. Consequently, repetitive applications are required for effective treatment. It would be desirable to provide a device which would provide maximum delivery of dermatological ingredients for local skin conditions as described above.

In particular, Scholl, U.S. Pat. No. 2,098,312 purports to describe a pad for medicating or treating sensitive places on the human foot, such as corns, calluses, bunions, and chafed areas. These pads may be composed of a plurality of adhesively united and superimposed plies of fabric or other flexible material.

Additional improvements in this area are described in Scholl, U.S. Pat. No. 2,115,237, which purports to describe a medicated button or pad for attachment directly to the body of a user. It appears to be particularly directed to the treatment of corns, calli, and similar afflictions. As described more generally, above, this device provides a limited quantity of medication to the treatment area.

Finally, Devillez, U.S. Pat. No. 5,641,507 purports to describe a delivery system for the administration of low viscosity cosmetic and dermatological ingredients without the use of plasters or repetitive applications. The system claims to eliminate migration of the low viscosity application liquid to areas where treatment is not required and/or sensitive areas of the patient's body which could be adversely affected if contacted by the application liquid.

SUMMARY OF THE INVENTION

Further objects and advantages of the invention will be readily apparent to those skilled in the art from the following detailed description, taken in conjunction with the sheets of drawings.

In particular, applicants have developed a layered delivery system for a skin care composition. The system includes a flexible cover layer forming an upper surface of the delivery system removably attached to a coupling layer, a first adhesive layer disposed on a lower surface of the delivery system, and a reservoir associated with the flexible cover layer. The coupling layer has an upper surface in facing relation to the flexible cover layer, an opposite lower surface, an outer perimeter, and defining an interior void volume substantially closed by the flexible cover layer, and the first adhesive layer is protected by a removable release liner. The reservoir is disposed in fluid communication with the interior void volume, and it carries the skin care composition.

In another aspect, the present invention relates to methods for providing multiple doses of a composition to a skin care area. The method includes the steps of applying to the skin a layered delivery system. The system includes a flexible cover layer forming an upper surface of the delivery system removably attached to a coupling layer, a first adhesive layer disposed on a lower surface of the delivery system, and a reservoir associated with the flexible cover layer. The coupling layer has an upper surface in facing relation to the flexible cover layer, an opposite lower surface, an outer perimeter, and defining an interior void volume substantially closed by the flexible cover layer, and the first adhesive layer is protected by a removable release liner. The reservoir is disposed in fluid communication with the interior void volume, and it carries the skin care composition. The outer perimeter of the coupling layer surrounds a desired skin care area, the skin care area is in facing relation to the interior void volume, and the first adhesive layer attaches the layered delivery system to the skin. The first composition is released from the first reservoir to the interior void volume whereby the composition is in fluid communication with the skin care area. The first flexible cover layer and first reservoir are removed from the layered delivery system while the first adhesive maintains the coupling layer to the skin and a second flexible cover layer and second reservoir associated therewith substantially the same as the first flexible cover layer and first reservoir is applied to the upper surface of the coupling layer. A second composition is thereafter released into the interior void volume.

BRIEF DESCRIPTION OF THE DRAWINGS

An embodiment of this invention will now be described in greater detail, by way of illustration only, with reference to the accompanying drawings, in which.

DETAILED DESCRIPTION OF THE INVENTION

The present invention relates generally to dermal, transdermal, mucosal or transmucosal ingredient delivery systems. Such devices are designed to deliver ingredients to the skin or exposed mucosa of a subject. The device is referred to "dermal" or "transdermal," as a function of whether or not the ingredients are formulated in such a way as to remain on the user's skin and be active there, or pass through the skin. The same distinction applies with respect to "mucosal" or "transmucosal" devices, but with reference to an exposed mucosal layer.

Devices for transdermal or percutaneous drug delivery and devices are typically characterized by delivering an amount of a drug or other ingredients, e.g., nitroglycerin, estrogen, estradiol, corticoid, levonorgestrel, etc. to the patient's skin at a rate controlled by the device. In a transdermal or transmucosal device, the drug is delivered systemically to the intended site of treatment within the body. Although effective for their intended use, such controlled release devices have limited utility for providing the kind of treatment which requires maximum delivery of the drug or active ingredient for local skin conditions, for example, lesions or abnormal skin features such as corns, warts, calluses, bunions, actinic keratoses and hard hyperkeratotic skin as is often found on the face, arms, legs or feet.

Figure 1:
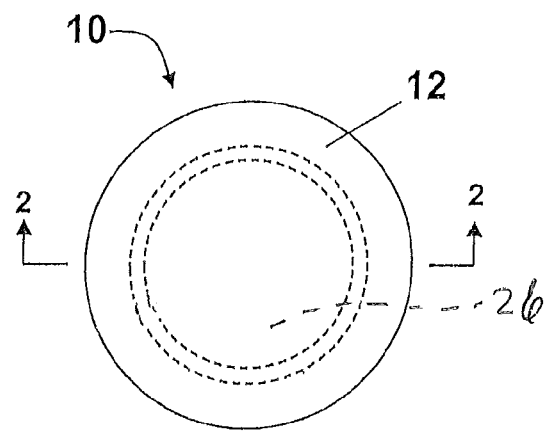
FIG. 1 is a top plan view of a first embodiment of a layered delivery system of the present invention.
Figure 2:
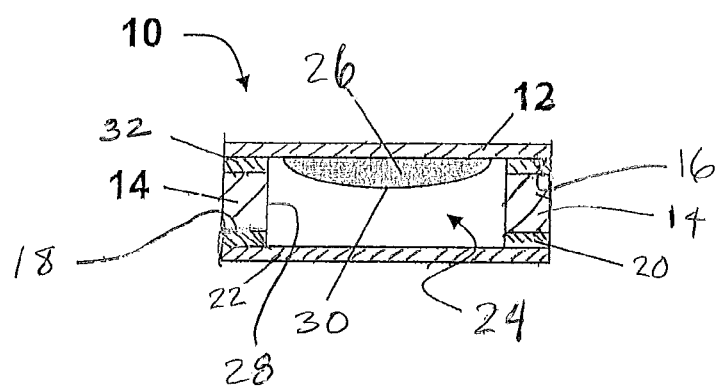
FIG. 2 is a cross-sectional view of the layered delivery system of FIG. 1 taken along the 2-2 plane.

FIGS. 1 and 2 illustrate a first embodiment of a layered delivery system (or device) of the present invention. Delivery system 10 comprises flexible cover layer 12 forming an upper surface of the delivery system, coupling layer 14 with an upper surface 16 and a lower surface 18, a first adhesive layer 20 associated with the lower surface 18 and release liner 22 protecting the first adhesive layer until use.

FIG. 2 is a cross-sectional view of delivery system 10 taken along the 2-2 plane. The figure shows flexible cover layer 12 and sidewalls 28 of coupling layer 14 are disposed in a manner to form an interior void volume, such as a chamber 24. Reservoir 26 is disposed in chamber 24.

Flexible cover layer 12 of delivery system 10 may have various shapes, such as, but not limited to rectangular, square, oval, circular, ovoid, or oblong. The shape of delivery system 10 is generally defined by the shape of flexible cover layer 12. Flexible cover layer 12 may be thin, highly flexible or deformable, water-impervious, and clear or opaque. In general, the thickness of flexible cover layer 12 should fall within the range of 0.05 to 0.20 millimeter to achieve the forming and flexing characteristics desired.

It is desired for the material used in flexible cover layer 12 to be both conformable to the contours of the body, and flexible so as to permit free movement of the body part wearing the product. Further, flexible cover layer 12 could be lightweight, and may be elastic (elastomeric) in character. It can be a woven or nonwoven. It can be a fabric, a film or a foam. Materials for use in flexible cover layer 12 include polyolefin (such as polyethylene) film or foam, polyurethane film or foam, and polyvinylchloride film or foam. Other examples of backings include, but are not limited to, non-woven backing materials such as polyurethane or elastomeric polyester materials and the like, or knitted or woven fabrics such as cotton, polyester, rayon and the like.

A polyethylene film may be used as flexible cover layer 12, and particularly effective results can be achieved with stretchable, elastomeric films formed of polyurethane, which has the further advantage of gas (including water vapor) transmissibility. It is to be understood, however, that other flexible, water insoluble polymeric films known in the art may be used. Furthermore, flexible cover layer 12 may be formed from closed-cell polymeric foam, particularly one with an integral skin covering the side facing away from the skin of the user. Foam layers formed of polyurethane or polyethylene are suitable, while other polymeric foams having similar properties may be used. In addition, flexible cover layer 12 may be made from other polyolefins, vinyl polyethylene acetate, textile non-woven fabrics, rubber, or other materials known in the adhesive article art. Polymers used to make flexible cover layer 12 used in bandages of the present invention may exhibit viscosity of about 500 to 500,000 centipoises at temperatures of about 190° C., or about 1,000 to 30,000 centipoises at temperatures of about 190° C., or about 3,000 to 15,000 centipoises at temperatures of about 190° C. Flexible cover layer 12 may be impermeable to liquid, but permeable to gas, which allows the wound and the skin to which delivery system 10 of the present invention is adhered to breathe. In one embodiment, flexible cover layer 12 may have pores of such a size that will allow only the passage of gases, which have molecules of extremely small size. Finally, one can conceive of a flexible cover layer that is perforated for more ventilation of the skin. Perforations may be circular in area and have a range of diameters, such as from about 0.1 to about 0.8 millimeters. However, flexible cover layer 12 may be totally impermeable to gases, when necessary.

Coupling layer 14 of delivery system 10 has an upper surface 16 in facing relation to the flexible cover layer 12 and an opposite, lower surface 18, directed toward the skin in use. Coupling layer 14 has an outer perimeter that may be in the form of various shapes, such as, but not limited to rectangular, square, oval, circular, ovoid, or oblong. The interior of the coupling layer 14 is open, and the sidewalls 28 and the inner surface of the flexible cover layer 12 cooperate to define the void volume or chamber 24. The shape of coupling layer 14 may match the shape of flexible cover layer 12, or the pad may be sized to be smaller in cross sectional area than the flexible cover layer 12. Coupling layer 14 may be highly flexible or deformable, water-impervious, and clear or opaque. In general, the thickness of coupling layer 14 should fall within the range of about 0.5 to about 10 millimeter, or about 1 to about 5 millimeter, or about 2 to about 3 millimeter, or to achieve the cushioning characteristics desired and to achieve the desired volume of chamber 24.

Coupling layer 14 may function as padding for the skin area to which delivery system 10 is applied. When used as padding, materials for use in coupling layer 14 include, but are not limited to, open or closed cell, microporous polyurethane foams, memory cushion made from Nitryl PVC rubber, latex foams, sponge rubber (commonly known as EPDM or Ethylene Propylene Diene Monomer), wool based felt, and comfort gels. Alternatively, coupling layer 14 may not be a material which provides padding. These materials include ceramics, metals, glasses, and stiff polymers.

As shown in FIG. 2, reservoir 26 is disposed in chamber 24 of delivery system 10. The reservoir 26 is associated with the cover layer 12. Reservoir 26 may have any structure capable of carrying the skin care composition. For example as shown in FIG. 2, reservoir 26 is a flexible sac disposed on an inner surface of the cover layer. Alternatively, the reservoir may be a porous structure impregnated with the skin care composition. When an outer wall 30 of sac (reservoir 26) is disrupted, the skin care composition carried thereby is able to pass into the interior void volume (chamber 24).

Sac wall 30 may be made of a material that is able to be disrupted, such as, for example, a thin polyethylene (LDPE) film or in the form of a gel. In some embodiments, flexible cover layer 12 may be of the same or different material and continuous with sac wall 30, it may also be achieved by applying heat, pressure, resin, or reactant to cause flexible cover layer 12 to physically, mechanically, chemically, electrically, or magnetically bind to sac wall 30. The binding of flexible cover layer 12 and sac wall 30 may also be achieved by ultrasonic welding, stitching, weaving, or winding a filament or fiber through both flexible cover layer 12 and sac wall 30. The binding of flexible cover layer 12 and sac wall 30 may still yet be achieved by having a fibrous mesh interweave between both flexible cover layer 12 and sac wall 30. Flexible cover layer 12 may also be mechanically integrated into sac wall 30, such as being held in a slot or vice structure incorporated into flexible cover layer 12. In other embodiments, reservoir 26 may comprise polymeric gels or glasses. Other embodiments may comprise two or more reservoirs 26, which, in some embodiments, may comprise multiple ingredients which interact with each other when they are mixed.

Release liner 22 is disposed on a lower surface of the layered delivery system 10 and protects the first adhesive layer 20, prior to use. In general, the thickness of release liner 22 should fall within the range of about 0.05 to 0.20 millimeter, and may be any sheet material having these properties such as paper, polyethylene and polypropylene. A suitable release material, for example, is a 40 to 75 pound basis weight paper coated on one or both sides with a suitable finish such as clay and with a release agent such as silicone.

Delivery system 10 comprises flexible cover layer 12 with a first and second surface, coupling layer 14 with an upper surface 16 and a lower surface 18, and release liner 22 with a first and second surface.

As shown in FIG. 2, a first adhesive layer 20 is associated with (e.g., disposed on) the lower surface 18 of flexible coupling layer 14 and is protected by a release liner 22. A second adhesive layer 32 is disposed between the upper surface of coupling layer 14 and the inner surface of the cover layer 12. Preferably, the second adhesive layer is associated with the cover layer 12 such that when such cover layer is removed from the upper surface 16 of the coupling layer 14, the upper surface 16 of the coupling layer 14 is relatively adhesive-free and ready for the application of another adhesive-coated cover layer 12.

Release liner 22 is sized and shaped to cover first adhesive layer 20.

In general, any of a variety of pressure-sensitive adhesives can be utilized as adhesive layers 20 and 32. In particular, pressure-sensitive adhesives that are biocompatible with human skin are typically utilized. In some embodiments, an adhesive of the present invention may also be either generally water soluble or generally insoluble, or dispersible in an aqueous environment. For instance, commercially available dispersible pressure-sensitive adhesive is sold under the trade name of HL-9415-X and is available from H.B. Fuller Company. Another suitable adhesive includes about 10-75% by weight of a polyalkyloxazoline polymer, 10-75% by weight of a functional diluent comprising a hydroxy compound or a carboxylic acid compound, and 5-50% by weight of a tackifier.

Adhesive layers 20 and 32 may comprise hydrocolloids. The hydrocolloid element used may be any substance that has a good performance in this utilization, as for example, sodium carboxymethylcellulose, pectin, xanthan gum, polysaccharides, sodium or calcium alginates, chitosan, seaweed extract (cageenan), polyaspartic acid, polyglutamic acid, hyaluronic acid or salts and derivatives thereof, among others.

Hydrocolloids, just as sodium carboxymethylcellulose and pectin, among others, are agents that form gels as soon as they come into contact with the bodily fluids from the wound. When used in adhesive bandages, these hydrocolloids are combined with elastomers and/or adhesives. Preferably, the adhesive bandage should guarantee a humid environment but without saturation, cicatrisation, which is a situation suitable for acceleration of the healing.

Adhesive layers 20 and 32 may be any conventional adhesive known for such use, as for example pressure acrylic adhesives, among others. Adhesive layers 20 and 32 need not be the same adhesive, or formulated similarly. Additionally, such an adhesive may contain a resin for increasing adhesion, a cohesion increasing agent, an absorption agent (preferably a polyacrylate superabsorbent, a polyacrylate salt superabsorbent or a mixture thereof), a plasticizer and optionally a pigment. The adhesive layer may further be configured in discontinuous patterns, arranged in lines, screen, spray or any other which a person skilled in the art understands as discontinuous.

Adhesive layer 32 is preferably formulated so that the flexible cover layer 12 can be removed while the remainder of the layered delivery system 10 (e.g., first adhesive layer 20 and coupling layer 14) remains adhered in place. A new flexible cover layer 12 with an intact reservoir 26 can be placed on the coupling layer 14.

Figure 3:
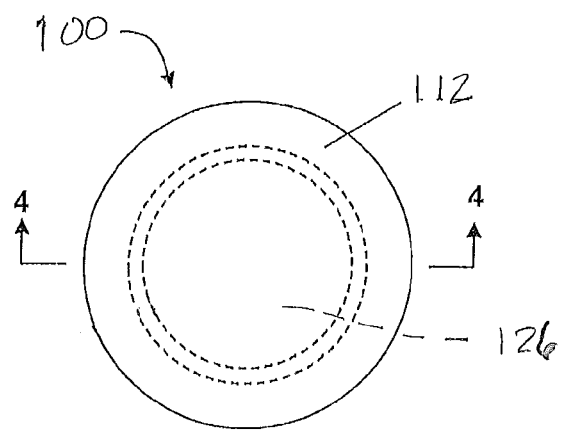
FIG. 3 is a top plan view of a second embodiment of a layered delivery system of the present invention.
Figure 4:
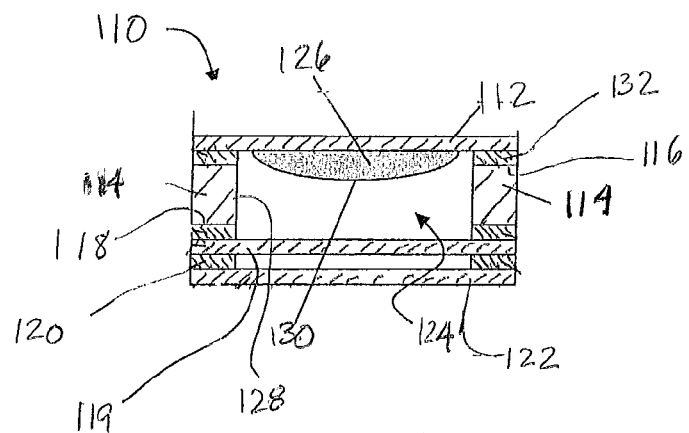
FIG. 4 is a cross-sectional view of the layered delivery system of FIG. 3 taken along the 4-4 plane.

FIGS. 3 and 4 illustrate a second embodiment of delivery system of the present invention. Here, the layered delivery system has the first adhesive layer coupled to the lower surface of the coupling layer through at least one intermediate layer. Delivery system 100 comprises flexible cover layer 112 forming an upper surface of the delivery system, coupling layer 114 with an upper surface 116 and a lower surface 118, a membrane 119, a first adhesive layer 120 associated with the membrane 119, and release liner 122 protecting the first adhesive layer until use.

FIG. 4 is a cross-sectional view of the delivery system of FIG. 3 taken along the 4-4 plane. The figure shows a flexible cover layer 112 and sidewalls 128 of coupling layer 114 that are disposed in a manner to form an interior void volume, such as a chamber 124. Reservoir 126 is disposed in chamber 124. As shown in FIG. 4, reservoir 126 is disposed on second surface of flexible cover layer 112, and has reservoir wall 130.

Flexible cover layer 112 of delivery system 100 has a first surface facing away from the skin and a second surface, opposite the first surface, and facing the skin. Flexible cover layer 112 may have various shapes, as discussed above, may be sized as discussed above, and may be formed of the materials discussed above.

Coupling layer 114 of delivery system 100 has an upper surface 116 in facing relation to the flexible cover layer 112 and an opposite, lower surface 118 directed toward the skin in use. Coupling layer 114 may have various shapes, as discussed above, may be sized as discussed above, and may be formed of the materials discussed above.

Membrane 119 of delivery system 100 is disposed between the coupling layer 114 and the first adhesive layer 120. Membrane 119 may have various shapes, such as, but not limited to rectangular, square, oval, circular, ovoid, or oblong. The shape of membrane 119 may correspond to the shape of flexible cover layer 112, or may correspond to the shape of the outer diameter of the coupling layer 114, or the shape of membrane 119 may correspond to the perimeter of the void volume or chamber formed by the coupling layer 114. Membrane 119 may also be sized to any shape of size between those described. Membrane 119 may be highly flexible or deformable, and clear or opaque. In general, the thickness of membrane 119 should fall within the range of about 0.05 to 1.0 millimeter to achieve the forming and flexing characteristics desired.

As shown in the embodiment of FIGS. 3-4, an upper surface of the membrane 119 is attached to the lower surface 118 of the coupling layer 114, and the first adhesive layer 120 is disposed on the lower surface of the membrane 119. Of course, one of ordinary skill will recognize that there may be additional elements between these layers.

The membrane 119 may be attached to the coupling layer 114 through an adhesive or other physical, mechanical, chemical, electrical, or magnetic bond to coupling layer 114. The bonding of membrane 119 and coupling layer 114 may also be achieved by ultrasonic welding, stitching, weaving, or winding a filament or fiber through both membrane 119 and coupling layer 114. The bonding of membrane 119 and coupling layer 114 may still yet be achieved by having a fibrous mesh interweave between both membrane 119 and coupling layer 114. Membrane 119 may also be mechanically integrated into coupling layer 114, such as being held in a slot, clasp, clamp, or vice structure incorporated into coupling layer 114. The bonding of bonding of membrane 119 and coupling layer 114 is shown as a construction adhesive layer 131 in FIGS. 4-6, Membrane 119 should be permeable to the skin care composition carried by the reservoir 126. Materials for use in membrane 119 can be polymeric, and in the form of a fabric, a film or an open foam. Membrane 119 may also be adhesive in nature. In some embodiments, the membrane 119 may be partially or wholly saturated with, or otherwise contain, a skin care composition. This may be the same or different than the skin care composition carried by reservoir 126. Thus, membrane 119 may contact the target region with an initial dose of a skin care composition prior to the release of the skin care composition by the reservoir 126.

As in the embodiment of FIGS. 1 and 2, a release liner 122 is disposed on a lower surface of the layered delivery system 100 and protects the first adhesive layer 120, prior to use. Release liner 122 may have various shapes as discussed above, may be sized as discussed above, and may be formed of the materials discussed above.

A second adhesive layer 132 is disposed between the upper surface 116 of coupling layer 114 and the inner surface of the cover layer 112. Preferably, the second adhesive layer 132 is associated with the cover layer 112 such that when such cover layer is removed from the upper surface 116 of the coupling layer 114, the upper surface 116 of the coupling layer 114 is relatively adhesive-free and ready for the application of another adhesive-coated cover layer 112.

As mentioned above, any of a variety of pressure-sensitive adhesives can be utilized as adhesive layers 120 and 132. Further, the adhesives could be configured in discontinuous patterns, arranged in lines, screen, spray or any other which a person skilled in the art understands as discontinuous.

The dimensions of the layered delivery system will depend upon the desired use thereof. Typically, small skin care areas use dressings which have a minor axis (perpendicular to longitudinal dimension) of about 25 mm. Larger skin care areas may use dressings having a major axis (along a longitudinal dimension) of about 100 mm. Of course, a circular product will have substantially identical major and minor axes. Preferably, the minor axis is preferably at least about 5 mm, more preferably at least about 15 mm, and most preferably at least about 25 mm. A major axis preferably less than about 100 mm, more preferably less than about 70 mm, and most preferably less than about 40 mm.

Figure 5:
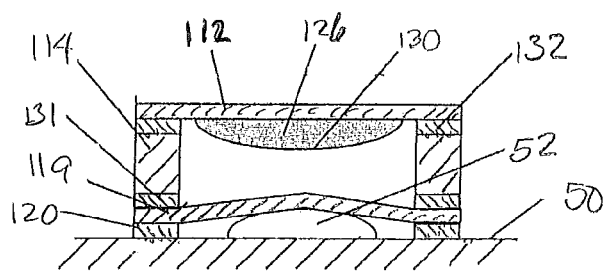
FIG. 5 is a cross-sectional view of the layered delivery system of FIG. 4 placed on the skin of a user prior to release of the active ingredient.
Figure 6:
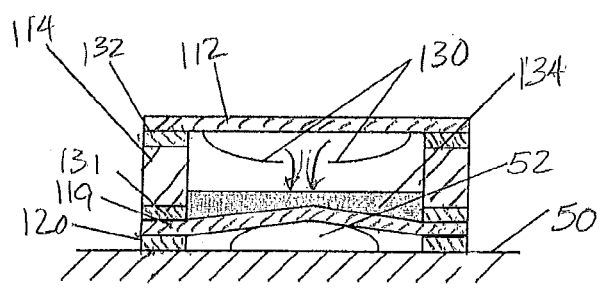
FIG. 6 is a cross-sectional view of the layered delivery system of FIG. 4 after disruption of the active ingredient pouch.

The system can deliver multiple doses of one or more compositions to a skin care area. FIGS. 5 and 6 show the use of the layered delivery system 100 of FIGS. 3 and 4 when applied to a user's skin. FIG. 5 is a cross-sectional view of layered delivery system 100 disposed on the skin 50 of a user prior to release of the first composition into the interior void volume. Delivery system 100 adheres to skin 50 via first adhesive layer 120. In this embodiment, membrane 119 is in contact with corn 52. Coupling layer 114 can act as a cushion to provide comfort to the user.

When wall 130 of reservoir 126 is ruptured, skin care composition (e.g., a composition containing an active ingredient to treat corns) is delivered into the interior void volume and then to skin 50. FIG. 6 shows that after the rupture, skin care composition 134 containing active ingredient is released from reservoir 126 into chamber 124 of delivery system 100, and is able to contact membrane 119. The skin care composition 134, or at least active ingredient(s) contained therein, is able to pass through membrane 119 and contact corn 52.

Wall 130 of reservoir 126 may be disrupted by the used by various means, including compression using a finger or several fingers, sharps (such as needles) in the coupling layer 114 or membrane 119, thermal melting, or chemical dissolution.

Delivery system 10, 100 described is ideally suited to deliver one or more active ingredients such as therapeutics to the surface of the skin. One or more active ingredients may be contained primarily or exclusively in reservoir 26, 126 of delivery system 10, 100. Illustrative classes of active ingredients that may be delivered to the skin via delivery system 10, 100 of the invention include, but are not limited to, active pharmaceutical ingredients (APIs), antibiotics, analgesics, antipyretics, antimicrobials, antiseptics, antiallergics, anti-acne, anesthetics, anti-inflammatories, hemostats, cooling agents, cosmetics, vitamins, vasodilators, emollients, pH regulators, antipruritics, counterirritants, antihistamines, soothing agents, and steroids. Specific active ingredients that may be delivered to the skin via the dressings of the invention include chlorhexidine, neomycin sulfate, polymyxin-B sulfate, zinc bacitracin, benzalkonium chloride, cetylpyridinium chloride, bupivacaine, tetracaine, cincaine, lidocaine, benzocaine, silver sulfadiazine, hydrocortisone, metandienone, trypsin, tolazoline, heparin, pramoxine, aloe vera, tretinoin, retinol, retinaldehyde, menthol, capsaicin, alpha hydroxy acids and vitamins such as Vitamin E.

In one embodiment, delivery system 10, 100 delivers active ingredients at high concentrations over short periods of time (i.e. ranging from about 0.1 hour to about 24 hours per wear). Some active ingredients at lower concentrations may be delivered for more than about 24 hours. In some embodiments, delivery system 10, 100 is capable of delivering a high concentrations of an active ingredient over an extended period of time and may remain adhered to skin 50 indefinitely or until desired. In other embodiments, delivery system 10, 100 is capable of delivering low concentrations of an active ingredient over a short period of time (i.e. ranging from about 0.1 hour to about 24 hours per wear). Active ingredients may be in liquid solution. In some embodiments, the active may be, but is not limited to, a liquid, a liquid solution, a foam, a gel, a sol, or in any form which may diffuse across membrane 119.

In some embodiments, delivery system 10, 100 may be used to treat the following conditions or to deliver the following active ingredients, the conditions and active ingredients including, but not limited to: warts (using salicylic acid, and/or other keratolytic agents); acne (using, for example salicylic acid, benzoyl peroxide, antibiotics, or other keratolytic agents); pain (using, for example, local anesthetics or non-steroidal anti-inflammatory drugs); moisturizers (using, for example, urea or water); finger and toenail beds (using, for example, urea, water, or anti-fungal agents); skin buffering (using, for example, buffering agents); vaccines (for example small pox, measles, flu, anthrax, or polio); poorly soluble drugs; larger molecular weight molecules (like about 500 to about 1500 molecular weight molecules such as heparin, LHRH); wound care (using water, debriding agent(s), or enzymes); or sampling and diagnostic agents (such as glucose, lactic acid, potassium, or allergens).

In some embodiments, the active ingredient preferably is one which can treat corns, warts or calluses. Preferably the active ingredient is a keratolytic agent such as salicylic acid or salts or esters thereof, glacial acetic acid, glycolic acid, phenoxyacetic acid, ascorbic acid, retinoic acid (tretinoin), fluorouracil, calcium pantothenate, cantharidin, podophyllum, phenol, zinc chloride, tannic acid, castor oil, or mixtures thereof. The amount of active ingredient in the liquid can range from about 1 to about 40 percent by weight, preferably from about 5 to about 30 percent. Preferably, the active ingredient is salicylic acid or a salt or ester thereof.

Suitable salts include the sodium, potassium, calcium or magnesium salts thereof. Suitable esters include the C-1 to C-4 esters thereof, such as methyl salicylate. Other esters include salsalate (salicylsalicylic acid), the salicylate ester of salicylic acid.

After delivery of the first composition to the skin care area is complete, the first flexible cover layer 12, 112 can be separated from the coupling layer 14, 114 while delivery system 10, 100 is disposed on skin 50. A new, second flexible cover layer 12, 112 with second reservoir 26, 126 associated therewith can be adhered to coupling layer 14, 114. Second reservoir 26, 126 can be ruptured and second composition can be delivered into interior void volume or chamber 24, 124. The second composition can be the same as or different to the first composition, and it will be recognized that additional flexible cover layer/reservoir combinations can be replaced in a like manner to deliver further skin care compositions to the skin care area. In some embodiments, delivery of additional flexible cover layers and reservoirs to the skin may be in compliance with a desired skin care regimen. In other embodiments, the skin care area may include at least one skin blemish and the composition comprises at least one active ingredient directed to the skin blemish.

The ingredients to be delivered may vary widely. They may be "drug" ingredients, oral care ingredients such as flavors, drugs, etc., or they could be cosmetic ingredients such as perfumes, creams or the like. The term "active" ingredient as used herein is intended to refer to the primary ingredient or ingredients to be delivered by the device, and is not intended to be used in its "FDA" sense as referring only to "drugs."

The present invention will be better understood from a consideration of the following illustrative examples.

EXAMPLES

In one example of the invention, a polyurethane film flexible cover layer 112 was used with a LDPE medicament reservoir 126. Deionized water was used as the active. A Bostick hot melt adhesive was used as adhesive layer 131 and adhesive layer 132. A closed cell polyurethane foam was used as coupling layer 114. An acrylic adhesive was used in adhesive layer 120. Membrane 119 consisted of an apertured polyurethane film.

In another example of the invention, a polyurethane film flexible cover layer 112 was used with a LDPE medicament reservoir 126. Deionized water was used as the active. A Bostick hot melt adhesive was used as adhesive layer 132. A closed cell polyurethane foam was used as the coupling layer 114. An acrylic adhesive was used in adhesive layer 131. Membrane 119 consisted of a hotmelt hydrocolloid adhesive, and adhesive layer 120 was not present.

While various embodiments of the invention have been set forth above, it will be apparent to those skilled in the art that various modifications and variations can be made in the present invention without departing from the scope or spirit of the invention. Thus, it is intended that the present invention cover such modifications and variations as come within the scope of the appended claims and their equivalents.

What is claimed is:

1. A layered delivery system for a skin care composition, the system comprising:
    a. a first flexible cover layer forming an upper surface of the delivery system removably attached to a coupling layer, the coupling layer having (i) an upper surface attached in facing relation to the first flexible cover layer, (ii) an opposite lower surface, (iii) an outer perimeter, (iv) and an open interior defined by coupling layer sidewalls, wherein the coupling layer sidewalls define an interior void volume substantially closed by the first flexible cover layer;
    b. a first adhesive layer disposed on a lower surface of the delivery system configured to be directed toward the skin during use and protected by a removable release liner; and
    c. a first reservoir comprising a sac having a rupturable wall and containing the skin care composition, the reservoir being attached to a lower surface of the first flexible cover layer and which extends therefrom into the interior void volume wherein said first reservoir is arranged and configured to dispense the skin care composition into the interior void volume and directly to the skin upon the rupture of the rupturable wall during use;
    wherein the first flexible cover layer and the attached first reservoir are removable from the coupling layer to permit the coupling layer to accommodate a second flexible cover layer and an attached second reservoir for a second dispensing of skin care composition.

2. The layered delivery system of claim 1 wherein the first adhesive layer is coupled to the lower surface of the coupling layer through at least one intermediate layer.

3. The layered delivery system of claim 1 wherein the first flexible cover layer is removably attached to the coupling layer through a second adhesive layer.

4. The layered delivery system of claim 1 wherein the first or second reservoir comprises a porous structure impregnated with the skin care composition.

5. The layered delivery system of claim 1 wherein the skin care composition comprises at least one active ingredient, at least one cosmetic ingredient, or combinations thereof.

6. A method of delivering multiple doses of one or more compositions to a skin care area comprising the steps of:
    a. Applying to the skin a layered delivery system comprising:
        i. A first flexible cover layer forming an upper surface of the delivery system removably attached to a coupling layer, the coupling layer having an upper surface in facing relation to the first flexible cover layer, an opposite lower surface, an outer perimeter, and defining an interior void volume substantially closed by the first flexible cover layer;

ii. A first adhesive layer disposed on a lower surface of the delivery system; and iii. A first reservoir associated with the flexible cover layer, disposed in fluid communication with the interior void volume, and carrying a first composition; Whereby the outer perimeter of the coupling layer surrounds a desired skin care area, the skin care area is in facing relation to the interior void volume, and the first adhesive layer attaches the layered delivery system to the skin;

b. Releasing the first composition from the first reservoir to the interior void volume whereby the composition is in fluid communication with the skin care area;

c. Removing the first flexible cover layer and first reservoir from the layered delivery system while the first adhesive maintains the coupling layer to the skin and applying a second flexible cover layer and second reservoir associated therewith substantially the same as the first flexible cover layer and first reservoir to the upper surface of the coupling layer; and d. Releasing a second composition from the second reservoir into the interior void volume.

7. The method of claim 6 further comprising repeating steps (c) and (d) with additional flexible cover layers and reservoirs in compliance with a desired skin care regimen.

8. The method of claim 6 wherein the skin care area includes at least one skin blemish and the composition comprises at least one active ingredient directed to the at least one skin blemish.

9. The method of claim 6 wherein the first and second compositions are substantially identical.

10. The method of claim 6 wherein the first and second compositions are substantially different.

\* \* \* \* \*